United States Patent [19]

Romancik et al.

[11] Patent Number: 5,917,032
[45] Date of Patent: Jun. 29, 1999

[54] CHEMICAL ACETYLATION OF DESACETYL-CEPHALOSPORINS

[75] Inventors: Guna Romancik, Jamesville; John J. Usher, East Syracuse, both of N.Y.

[73] Assignee: Bristol-Myers Squibb Company, Princeton, N.J.

[21] Appl. No.: 09/173,091

[22] Filed: Oct. 15, 1998

Related U.S. Application Data

[60] Provisional application No. 60/064,337, Oct. 30, 1997.

[51] Int. Cl.$^6$ .................................................. C07D 501/04
[52] U.S. Cl. .............................................................. 540/230
[58] Field of Search ............................................. 540/230

[56] References Cited

U.S. PATENT DOCUMENTS

| | | | |
|---|---|---|---|
| 3,532,694 | 10/1970 | Somerfield et al. | 540/230 |
| 5,221,739 | 6/1993 | Wildfeuer | 540/230 |
| 5,512,454 | 4/1996 | Usher | 435/47 |
| 5,552,542 | 9/1996 | Reid et al. | 540/217 |

FOREIGN PATENT DOCUMENTS

| | | |
|---|---|---|
| 153874 | 9/1985 | European Pat. Off. . |
| 230972 | 8/1987 | European Pat. Off. . |
| WO 90/12110 | 10/1990 | WIPO . |

OTHER PUBLICATIONS

G.G.F. Newton and E.P. Abraham, "Cephalosporin C, a New Antibiotic containing Sulphur and D–α–Aminoadipic Acid", *Nature*, 175, p. 548 (Mar. 26, 1955).

*Primary Examiner*—Mark L. Berch
*Attorney, Agent, or Firm*—Aldo A. Algieri

[57] ABSTRACT

The present invention is concerned with a chemical acetylation process for the preparation of 3'-acetylated cephalosporin from desacetyl-cephalosporin. The novel process is carried out with an acetyl donor and an activator or catalyst.

7 Claims, No Drawings

CHEMICAL ACETYLATION OF DESACETYL-CEPHALOSPORINS

CROSS REFERENCE TO RELATED APPLICATIONS

This nonprovisional application claims the benefit of copending provisional application U.S. Ser. No. 60/064,337, filed Oct. 30, 1997.

FIELD OF INVENTION

The invention provides a process for the direct chemical conversion of desacetyl-cephalosporins to 3'-acetylated cephalosporins by acetylation in an organic solvent with an acetyl donor in the presence of an activator or catalyst.

BACKGROUND OF THE INVENTION

3-Acetoxymethyl-7β-aminoceph-3-em-4-carboxylic acid (7-ACA) is of primary importance as a starting material for the preparation of semi-synthetic commercial cephalosporin antibiotics. This intermediate is produced commercially from cephalosporin C, a fermentation product of *Cephalosporin acremonium* (see Newton and Abraham, *Nature*, 175, 548, 1955), by hydrolysis of the D-α-aminoadipyl side chain, either chemically or enzymaticially. 3-Hydroxymethyl-7β-aminoceph-3-em-4-carboxylic acid (des-7-ACA) is usually produced as an unwanted side product in the preparation of 7-ACA caused by either the chemical or enzymic (esterase) hydrolysis of the 3-acetyl group. Des-7-ACA can be produced by the action of various esterases on 7-ACA. In addition, it can be produced from desacetyl-cephalosporin C by enzymic hydrolysis in a manner analogous to the conversion of cephalosporin C to 7-ACA (World Patent No. WO 90/12110). As a result of the highly reactive nature of the C-7 amino group, chemical synthesis of 7-ACA from the deacetylated precursor results in a mixture of products. The use of typical chemical acylating reagents such as acetyl chloride or acetic anhydride produces inter alia 7-ACA, N-acetyl 7-ACA and N-acetyl desacetyl 7-ACA. In addition, 3-hydroxymethyl-7β-aminoceph-3-em-4-carboxylic acids are susceptible to lactonization under these conditions. Prior art methods of O-acylation involve blocking the reactive C-7 amino group, then performing O-acylation in a non-polar, organic solvent in the presence of a 4-(tertiary amino) pyridine catalyst with an acid-acceptor base and then deblocking the C-7 amino group (European Patent No. 153,874A). Further methods comprise of esterifying the 4-position carboxyl group of the C-7 acylated compound to prevent lactonization during the reaction, and deesterifying the carboxy group and deprotecting the C-7 amino group to produce the 3-alkanoyloxymethyl-7β-aminoceph-3-em-4-carboxylic acid (U.S. Pat. No. 3,532,694), or performing the O-acylation in an aqueous medium in the presence of a 4-(tertiary amino)pyridine catalyst with an acid-acceptor base and then deblocking the C-7 amino group (European Patent No. 0230972). More recently, a chemical process for acetylating the 3-hydroxymethyl cephalosporins in an aqueous solvent has been described (U.S. Pat. No. 5,221,739), as well as the use of an enamine for the protection of the C-7 amino group (U.S. Pat. No. 5,552,542). Thus, it was unexpectedly discovered by the present inventors that the use of certain acetyl donors in the presence of an activator or catalyst can provide an efficient direct chemical acetylation of desacetyl-cephalosporin without the use of any protecting or blocking groups.

SUMMARY OF THE INVENTION

The present invention provides a process for the direct chemical conversion of desacetyl-cephalosporins to 3'-acetylated cephalosporins, in anhydrous or nearly anhydrous solution, by acetylation with an acetyl donor in the presence of dicyclohexylamine and an organic solvent. More specifically, the present invention provides a unique chemical process for the acetylation of des-7-ACA to 7-ACA.

DETAILED DESCRIPTION OF THE INVENTION

The present invention relates to an improved process for producing 3'-acetylated cephalosporins by a selective chemical acylation of the 3'-hydroxymethyl group of a desacetyl-cephalosporin. The process of the invention is illustrated in Reaction Scheme I by the direct chemical conversion of desacetyl-7-aminocephalosporanic acid (desacetyl-7-ACA) to 7-aminocephalosporanic acid (7-ACA) which is an important intermediate in the synthesis of many cephalosporin antibiotics.

REACTION SCHEME I

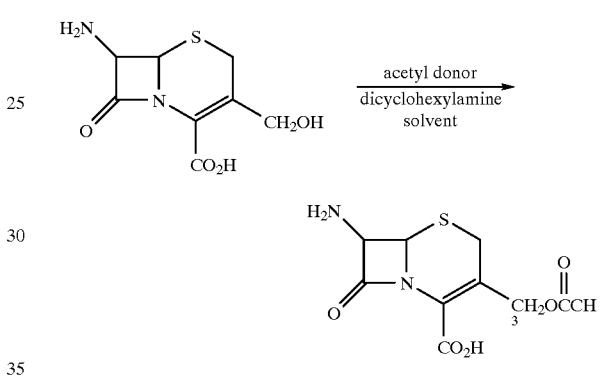

According to the process of this invention, the chemical acetylation desacetyl-7-ACA is advantageously carried out in an anhydrous, or almost anhydrous organic solvent or mixture of solvents, for example, N,N-dimethylformamide (DMF), dimethyl sulfoxide (DMSO), formamide, cyclohexanone, N,N-dimethylacetamide, ethanol, isopropanol, acetone, 1-methyl-2-pyrrolidinone, phenoxyethanol and the like. The acetylation reaction is carried out with various acetyl donors such as vinyl acetate, phenyl acetate, 1,1-diacetoxy-2-propene, 4-methylumbelliferyl acetate, isopropenyl acetate and the like in the presence of dicyclohexylamine (DCHA) as the activator or catalyst. It should be appreciated by those skilled in the art that in some cases such as when vinyl acetate is the acetyl donor, benzoic hydrazide or oxalyl dihydrazide may be used as an acetaldehyde scavenger.

Under varying reaction conditions the acetylation proceeds to 15–97% conversion of desacetyl-7-ACA in about 18 to 52 hours and produces as high as 80–90% "in solution" activity yields of the desired 7-ACA. Surprisingly, under the conditions described herein, there is very little or no synthesis of the undesired lactone or the N-acetylated products observed in reactions where sufficient DCHA is present. The desired 7-ACA is advantageously precipitated by acidification with acids such as hydrogen chloride, acetic acid, and sulfuric acid. Preferably, the 7-ACA is isolated using glacial acetic acid alone, or a mixture of glacial acetic and sulfuric acid. In some cases further purification is achieved by recrystallization from aqueous methanol or water. Final activity yields of 7-ACA are 40–70% with purities as high as 80–93%.

Various acetyl donors in reaction mixtures containing solutions or suspensions of 5% desacetyl-7-ACA in an organic solvent, for example, dimethylformide, dimethyl sulfoxide and methyl pyrrolidinone, plus dicyclohexylamine were tested. Reactions were carried out at room temperature for 21–23 hours and products were measured by HPLC. Specific examples of preferred acetyl donors include vinyl acetate, phenyl acetate, 4-methylumbelliferyl acetate, 1,1-diacetoxy-2-propene and isopropenyl acetate. Most preferred acetyl donors are vinyl acetate and phenyl acetate.

Several solvent studies were done using 5% desacetyl-7-ACA in reaction mixtures containing dicyclohexylamine+phenyl acetate+solvent in equal volumes and are described herein in the examples. Each of these reactions were held at room temperature, and the conversion of desacetyl-7-ACA to 7-ACA was measured by HPLC. Preferably the solvents are selected from ethanol, isopropanol, acetone, dimethylformamide, formamide, cyclohexanone, dimethyl sulfoxide, dimethylacetamide, methyl pyrrolidinone and phenoxyethanol.

At 23 hours some of the reaction mixtures remained soluble while others became suspensions or gelled solids. As described herein, several reactions were carried out to combine the solubility properties of the preferred solvents, i.e., cyclohexanone, formamide and dimethyl sulfoxide, with other solvents to find a combination of two solvents that would give both soluble reaction mixtures and good conversions. Most preferably, the acylation of des-7-ACA is carried out in a solvent or a mixture of two solvents which will provide a soluble 1 or 2 phase reaction mixture.

The methods which constitute this invention and the compounds prepared will appear more fully from a consideration of the following examples which are given for the purpose of illustration only and are not to be construed as limiting the invention in sphere or scope.

DESCRIPTION OF SPECIFIC EMBODIMENTS

Method for HPLC Assay of 7-ACA and Desacetyl-7-ACA

HPLC System

Column: Spherisorb ODS2, 50 mm, Keystone Scientific, Inc.

Detection: 254 nm

Flow Rate: 4.0 ml/min.

Injection Volume: 5 μl

Temperature: ambient

Mobile Phase Preparation 1.946 g Sodium 1-octane-sulphonate (Lancaster Synthesis), 810 ml deionized water, 90 ml methanol, 900 μl phosphoric acid (85% stock solution)

| Relative Retention Times | |
|---|---|
| N-Acetyl-desacetyl-7-ACA | 0.32 |
| Desacetyl-7-ACA | 0.64 |
| N-Acetyl-7-ACA | 0.80 |
| 7-ACA lactone | 1.40 |
| 7-ACA | 2.20 |
| Desacetoxy-7-ACA | 3.49 |
| "Unknown" Product | 5.37 |

General Procedure for Conversions of Desacetyl-7-ACA to 7-ACA

Combine together dicyclohexylamine (DCHA), a solvent (such as in Example 6, Table 1 and Example 7, Table 2), and an acetyl donor (vinyl acetate, phenyl acetate, 1,1-diacetoxy-2-propene, 4-methylumbelliferyl acetate or isopropenyl acetate) at room temperature, and then add the acetaldehyde scavenger (benzoic hydrazide or oxalyl dihydrazide), in some cases where vinyl acetate is the acetyl donor. Add desacetyl-7-ACA and stir continuously throughout the reaction. Chill the mixture to 5–100° C. for best stability of product, or proceed at room temperature for a faster reaction. The reaction may take 18 to 52 hours to reach maximum conversion to 7-ACA, depending on the solvent, donor, DCHA concentration, and temperature used.

The concentration of 7-ACA was monitored by taking small samples of uniform whole mixture, diluting 100× into a solution of 50% aqueous acetonitrile, and assaying the diluted samples immediately by HPLC. Resulting pH of samples thus diluted in aqueous acetonitrile is about 9–10, and is typically referred to as the pH of the reaction.

Precipitation and Isolation of 7-ACA Following Acetylation of Desacetyl-7-ACA

When the amount of 7-ACA reaches a maximum level, the reaction mixture is chilled to 5–100° C. and at least 1–1.5 volumes of glacial acetic acid, or glacial acetic acid plus concentrated sulfuric acid at about 0.4 and 0.02 volumes, respectively, is added to quickly drop the pH to about 3.5–4.0 and precipitate the 7-ACA. The pH adjustment is done rapidly to avoid formation of undesired by-products. Continue to stir the extraction mixture until the 7-ACA concentration in the supernatant remains constant or is less than 4% of the 7-ACA concentration in the whole mixture. (Acidic samples, which may not be soluble in 50% aqueous acetonitrile, must first be neutralized in buffer before diluting for assay by HPLC.) The precipitate is collected by filtration and the cake washed with a small amount of 50/50 mixture of glacial acetic acid and solvent similar to that used in the acetylation reaction. Either wash the 7-ACA cake with acetone and dry in an evaporator, or proceed directly to the recrystallization steps.

Further Purification of 7-ACA by Recrystallization

The 7-ACA solid isolated above is added to distilled water equivalent to about 40%–100% of the volume of the original conversion reaction, and the 7-ACA is dissolved by rapid stirring and slow addition of concentrated ammonia to about pH 7.0–8.0. The 7-ACA solution is advantageously filtered to remove any undissolved solids, such as residual oxalyl dihydrazide. The clear solution is chilled to 5–100° C. and the pH adjusted to 3.5–4.0 with 6N HCl, or alternatively, an equal volume of methanol is added before adjusting the pH, and continue to chill while stirring until the concentration of 7-ACA in the supernatant reaches a minimum level. Collect the 7-ACA by filtration, wash the cake with a small amount of glacial acetic acid followed by a small amount of distilled water and a small amount of acetone. Dry the 7-ACA in an evaporator to constant weight.

Acetylation of Desacetyl-Cephalosporin to 3'-Acetylated Cephalosporin

EXAMPLE 1

9.0 ml Dimethyl Sulfoxide 1.0 ml Dicyclohexylamine 0.75 g 4-methylumbelliferyl Acetate 0.5 g Desacetyl-7-ACA Dimethyl sulfoxide and dicyclohexylamine were combined and 4-methylumbelliferyl acetate was added. The mixture was stirred at room temperature until partly dissolved, and then desacetyl-7-ACA was added to start the reaction. The mixture was stirred at room temperature for 21 hours and assayed by HPLC. The yield of 7-ACA was approximately 60%, as measured by area percent, and 26% of the desacetyl-7-ACA remained.

EXAMPLE 2

40.0 ml Ethanol 40.0 ml Dicyclohexylamine 20.0 ml Phenyl Acetate 5.0 g Desacetyl-7-ACA Ethanol and dicyclohexylamine were combined, phenyl acetate was stirred in, and then desacetyl-7-ACA was added to start the reaction. The mixture was stirred at room temperature for 30 hours and assayed by HPLC. The yield of 7-ACA was approximately 86%, and 9% of the desacetyl-7-ACA remained.

EXAMPLE 3

20.0 ml Dimethylformamide 15.0 ml Dicyclohexylamine 1.5 g Benzoic Hydrazide 2.0 g Desacetyl-7-ACA 5.0 ml Vinyl Acetate Dimethylformamide and dicyclohexylamine were combined, and then benzoic hydrazide and desacetyl-7-ACA were dissolved or dispersed in the mixture by the action of a tissue tearor (Biospec Products Inc.) for a few seconds. Vinyl acetate was added last to start the reaction. The mixture was stirred at room temperature for 18 hours and assayed by HPLC. The yield of 7-ACA was 94% and there was 3% of the desacetyl7-ACA remaining.

After 18 hours, the extraction of the reaction mixture was begun by stirring in 8 grams of crushed dry ice and 60 ml of glacial acetic acid. (The acid was first seeded with 20 mg of 7-ACA before adding to the reaction mixture.) The 7-ACA product was allowed to precipitate while stirring for 30 minutes. The mixture was filtered, washed on the filter with 40 ml of 50/50 glacial acetic acid and dimethylformamide and finally 60 ml of acetone. The solids were lyophilized and gave 71% activity yield of 7-ACA with a purity of about 90%.

EXAMPLE 4

5.0 ml Dimethyl Sulfoxide 1.0 ml Dicyclohexylamine 4.0 ml Vinyl Acetate 0.5 g Oxalyl Dihydrazide 0.5 g Desacetyl-7-ACA Dimethyl sulfoxide and dicyclohexylamine were combined, and then vinyl acetate was admixed, followed by the oxalyl dihydrazide. The mixture was stirred at room temperature for 15 minutes to dissolve some of the solids and then desacetyl-7-ACA was added to start the reaction. The mixture was stirred for 15 minutes at room temperature to allow desacetyl-7-ACA to dissolve, and then the reaction mixture was chilled to 5–100° C. and shaken at 200 rpm. At 18 hours the yield of 7-ACA was 92% by HPLC assay. After 19 hours, the mixture had a pH of about 9.5. The resulting pH of a 10 μl sample diluted 100× in 50% aqueous acetonitrile is typically referred to as the pH of the reaction. (The "in solution" yield of 7-ACA at this point was 92%.) After 19 hours, the 7-ACA was precipitated by rapid addition of 10 ml of glacial acetic acid, quickly dropping the pH of the mixture to about 3.5, and continuing to stir rapidly at 5–100° C. for about 45 minutes. The 7-ACA solids were collected by filtration and then dissolved immediately in 10 ml deionized water by careful addition of 10 N and 1 N ammonia to pH of 7.0–7.5. The solution was clarified by filtration to remove any undissolved solids, such as residual oxalyl dihydrazide, and the 7-ACA concentration was assayed by HPLC. The total yield of 7-ACA in solution before and after clarification was 85%. The clarified solution was then chilled to 5–100° C., and the pH adjusted to 3.5 with slow addition of 6N HCl to precipitate the 7-ACA. The solids were retained by filtration, washed with a small amount of DMSO followed by a rinse with acetone, and the 7-ACA solid was dried to a constant weight in an evaporator. Final yield of 7-ACA was 50% with a purity of 79% 7-ACA and 11 % desacetyl-7-ACA.

EXAMPLE 5

3.0 ml 1-methyl-2-pyrrolidinone 2.0 ml Dicyclohexylamine 5.0 ml Isopropenyl Acetate 1.0 g Desacetyl-7-ACA Methyl pyrrolidinone and dicyclohexylamine were combined, isopropenyl acetate was stirred in, desacetyl-7-ACA was added last and the mixture was stirred at room temperature for 18 hours. The mixture was assayed by HPLC, and 6% of the original chromatographic area of desacetyl-7-ACA had been converted to 7-ACA.

EXAMPLE 6

Acetylation of Des-7-ACA to 7-ACA with Phenyl Acetate as Acetyl Donor and Various Solvents Solvent studies were done using 5% desacetyl-7-ACA in reaction mixtures containing dicyclohexylamine+phenyl acetate+solvent in equal volumes. These reactions were held stationary at room temperature, and conversions of desacetyl-7-ACA to 7-ACA were measured by HPLC. The results are reported below in Table 1.

TABLE 1

Conversions Using One Solvent
Solvent + DCHA + Phenyl Acetate
(1:1:1) + 5% Desacetyl-7-ACA

| Solvent | Conversion | 23 Hour Appearance |
| --- | --- | --- |
| Ethanol | 88% | Solid |
| Cyclohexanone | 72% | Soluble (1 phase) |
| Formamide | 53% | Soluble (2 phase) |
| Isopropanol | 64% | Suspension |
| Acetone | 73% | Solid |
| Dimethylformamide | 51% | Solid |
| Dimethyl sulfoxide | 65% | Soluble (1 phase) |
| Dimethylacetamide | 68% | Solid |
| Methylpyrrolidinone | 72% | Suspension |
| Phenoxyethanol | 81% | Suspension |

EXAMPLE 7

Acetylation of Des-7-ACA to 7-ACA Using Phenyl Acetate as Acetyl Donor and Two Solvents The following table shows reactions held stationary at room temperature for 23 hours, similar to Example 6, except that two solvents were used instead of one. All of the combinations eventually gave soluble reaction mixtures except dimethyl sulfoxide+ethanol or dimethyl sulfoxide+isopropanol, and all of the formamide conditions became two phase. The results are reported below in Table 2.

TABLE 2

Conversions Using Two Solvents
Solvent 1 + Solvent 2 + DCHA + Phenyl Acetate
(0.5:0.5:1:1) + 5% Desacetyl-7-ACA

| Two Solvent | | 23 Hr Conv. |
|---|---|---|
| Cyclohexanone | + Ethanol | 81% |
| | + Isopropanol | 78% |
| | + Acetone | 74% |
| | + Dimethylformamide | 58% |
| | + Dimethylacetamide | 55% |
| | + Methyl pyrrolidinone | 74% |
| | + Phenoxyethanol | 83% |
| Formamide | + Ethanol | 87% |
| | + Isopropanol | 81% |
| | + Acetone | 75% |
| | + Dimethylformamide | 86% |
| | + Dimethylacetamide | 87% |
| | + Methyl pyrrolidinone | 85% |
| | + Phenoxyethanol | 71% |
| Dimethyl sulfoxide | + Ethanol | 87% |
| | + Isopropanol | 83% |
| | + Acetone | 83% |
| | + Dimethylformamide | 77% |
| | + Dimethylacetamide | 72% |
| | + Methyl pyrrolidinone | 76% |
| | + Phenoxyethanol | 87% |

What is claimed is:

1. A process for the preparation of 7-aminocephalosporanic acid having the formula

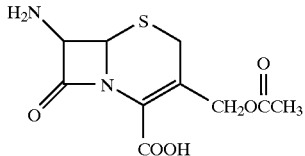

which comprises the steps of (a) reacting a compound of the formula

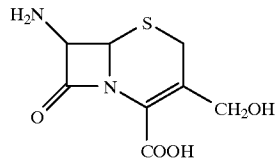

with an acetyl donor selected from the group consisting of vinyl acetate, phenyl acetate, 1,1-diacetoxy-2-propene, 4-methylumbelliferyl acetate, isopropenyl acetate; and dicyclohexylamine in an anhydrous organic solvent or mixture of organic solvents and (b) acidifying the reaction mixture to produce said 7-aminocephalosporanic acid.

2. A process of claim 1 wherein the acetyl donor is vinyl acetate.

3. A process of claim 1 wherein the acetyl donor is phenyl acetate.

4. A process of claim 1 wherein the organic solvent or mixture of organic solvents is selected from the group consisting of ethanol, cyclohexanone, formamide, isopropanol, acetone, dimethylformamide, dimethylsulfoxide, N,N-dimethylacetamide, 1-methyl-2-pyrrolidinone and phenoxyethanol.

5. A process of claim 4 wherein said mixture of organic solvents is selected from the group of two organic solvents consisting of ethanol, cyclohexanone, formamide, dimethylsulfoxide, isopropanol and acetone.

6. A process of claim 1 wherein the acid used in step (b) is glacial acetic acid or a mixture of glacial acetic acid and sulfuric acid.

7. A process of claim 1 wherein the reaction mixture in step (b) is acidified to about pH 3.5 to 4.0.

* * * * *